United States Patent [19]

Shimizu et al.

[11] Patent Number: 4,664,756
[45] Date of Patent: May 12, 1987

[54] METHOD OF DETECTING ELECTRODE POTENTIAL IN KARL FISCHER MOISTURE METER

[75] Inventors: Toshiyuki Shimizu; Yoshitomo Furukawa, both of Kyoto, Japan

[73] Assignee: Kyoto Electronics Manufacturing Co., Ltd., Kyoto, Japan

[21] Appl. No.: 686,868

[22] Filed: Dec. 27, 1984

[30] Foreign Application Priority Data

Jul. 7, 1984 [JP] Japan .................. 59-141202

[51] Int. Cl.$^4$ ............................ G01N 27/44
[52] U.S. Cl. .................... 204/1 T; 204/405; 422/75; 422/98; 436/42
[58] Field of Search ............. 436/42; 204/405, 1 T, 204/1 M, DIG. 8; 422/75, 98

[56] References Cited

U.S. PATENT DOCUMENTS

| 3,032,493 | 5/1962 | Coulson et al. | 204/405 |
| 3,835,008 | 9/1974 | Fisher et al. | 204/405 |
| 3,950,237 | 4/1976 | Arakawa et al. | 204/405 |
| 4,211,614 | 7/1980 | Eppstein et al. | 436/42 |
| 4,255,242 | 3/1981 | Freeman | 204/147 |
| 4,419,190 | 12/1983 | Dietz et al. | 204/425 |

OTHER PUBLICATIONS

Karlsson et al, "Talanta", (1971), vol. 18, pp. 459–465.

Primary Examiner—T. Tung
Attorney, Agent, or Firm—Armstrong, Nikaido, Marmelstein & Kubovcik

[57] ABSTRACT

A method of detecting an electrode potential in a Karl Fischer moisture meter comprises the step of subtracting an electrode potential which is caused by a liquid resistance of a liquid sample from an electrode potential which is generated in an end point detecting electrode in the Karl Fischer moisture meter, to thereby obtain a true polarization potential.

3 Claims, 4 Drawing Figures

METHOD OF DETECTING ELECTRODE POTENTIAL IN KARL FISCHER MOISTURE METER

BACKGROUND OF THE INVENTION

1. Field of the Invention

The present invention relates to a method of detecting a correct potential at the end point of titration having regard to an electrode potential caused by a liquid resistance of a liquid sample in a Karl Fischer titration for determining a small amount of water contained in the liquid sample.

2. Description of the Prior Art

Karl Fischer's method has been generally known as a method of determining a small amount of water contained in solids, liquids or gases. This is a kind of moisture determination based on the fact that water reacts quantitatively with iodine and sulfur dioxide gas in the presence of methyl alcohol and pyridine in accordance with the following equations:

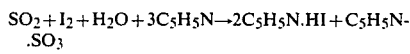

The end point of titration is accurately detected by the dead stop end point method in which two pieces of platinum electrode immersed in a liquid sample are polarized by allowing a minute electric current to flow therebetween and the change of potential caused by an excess of Karl Fischer reagent is detected.

A small amount of water contained in a sample has been determined as follows on the bsis of the above described principle: Referring to FIG. 2, numeral 1 designates a titration flask for use in the conventional Karl Fischer moisture meter in which a liquid sample (organic solvent+sample) is put and the titration is carried out by running Karl Fischer reagent thereinto. The titration flask 1 is provided with an injection port 2 of Karl Fischer reagent and two pieces of platinum electrode 3 for detecting the end point of titration, the opening port being closed with a rubber stopper 4. An appointed quantity of a liquid sample is injected into the titration flask 1 through a syringe 5, of which pointed end needle portion runs through the rubber stopper 4, so as not to bring the liquid sample into contact with the atmospheric moisture, preventing any change in quantity of water in the liquid sample.

At first, a direct current signal, a low-frequency alternating current signal or a pulse signal is applied to the platinum electrodes 3 and an electric potential, which is produced between the electrodes 3, is measured. When the water contained in the liquid sample is in excess, the polarization potential of the platinum electrodes 3 is raised (polarized state), resulting in a poor flow of an electric current. Then, Karl Fischer reagent gradually becomes excessive with the consumption of water as a result of the titration, whereby the polarization potential of the platinum electrodes 3 is lowered (depolarized state), and an electric current flows easily. That is to say, the water is gradually consumed with the titration until it is exhausted, whereupon an electrode potential undergoes a sudden change. The concentration of water contained in the liquid sample can be determined from the quantity of Karl Fischer reagent used for the titration up until the sudden change of the electrode potential takes place. The titration curve showing the electrode potential plotted against the concentration of Karl Fischer reagent is drawn with the dotted curve $C_1$ in FIG. 3. In the titration, it is only necessary to presume the curve $C_1$, set the end point potential $V_1$, and run Karl Fischer reagent into the liquid sample until the end point potential $V_1$ is reached.

An electrode potential of the platinum electrodes 3 not only undergoes a change at the time when the liquid sample turns from a water-excesss state to a Karl Fischer reagent-excess state but also depends upon the liquid resistance of the liquid sample. Assuming that the liquid resistance of the liquid sample is a constant and gives rise to a voltage drop $V_2$ as shown in FIG. 3, an electrode potential does not become lower than $V_2$ and the titration curve, curve $C_2$ in this case, lies above a straight line $V_2$. As a result, even though Karl Fischer reagent becomes excessive in the liquid sample, an electrode potential does not come down to the end point potential $V_1$, whereby the determination becomes impossible. Therefore, measures such as the adjustment of the setting of the end point potential or the selection of lower resistant organic solvents as a constituent of the liquid sample can be taken. But, both of them are unsatisfactory from the standpoint of operability in that the adjustment or the selection should be made for every sample. In addition, even though the setting of the end point potential $V_1$ is adjusted as above described, the liquid resistance of the liquid sample can change in the course of titration. For example, where the voltage caused by the liquid resistance varies dependent upon the concentration of Karl Fischer reagent—that is, as the titration progresses—the voltage curve becomes that illustrated by the curve $V_3$ in FIG. 4. The titration curve showing the change of an electrode potential is the curve $C_3$, and the curve obtained by subtracting the voltage $V_3$ from an electrode potential, that is the curve $C_1$, is the original titration curve.

Accordingly, the concentration $D_3$ of Karl Fischer reagent at the end point potential $V_1$ obtained from the curve $C_3$ deviates from the original concentration $D_1$ of Karl Fischer reagent at the end point potential $V_1$ obtained from the curve $C_1$, leading to an error in the result.

SUMMARY OF THE INVENTION

The present invention is designed to detect a true polarization potential and to that end comprises the steps of detecting an electrode potential generated in an end-point detecting electrode in a Karl Fischer moisture meter and subtracting an electrode potential caused by a liquid resistance from the detected electrode potential to obtain the true polarization potential.

DETAILED DESCRIPTION OF THE PREFERRED EMBODIMENT

One embodiment of the present invention is based on the following measurement principle: Assuming that R stands for a liquid resistance and v the true polarization potential in the case where a constant direct current $i$ and a constant alternating curent $\underline{i}$ for detecting a liquid resistance are applied to the platinum electrodes 3 simultaneously, the potential $V_1$ resulting from $\underline{i}$ is given by the equation $V_1 = v + \underline{i} \cdot R$. That is, it is the sum of the true polarization potential v and a potential i·R resulting from the liquid resistance R. In addition, the potential $V_2$ resulting from i is a potential (i·R) due to the liquid resistance R, and is given by the equation $V_2 = i \cdot R$. Therefore, $V_1 - V_2 = v + i \cdot R - i \cdot R = v + R(i - i)$. If $\underline{i}$ is set equal to i, $V_1 - V_2 = v$. Accordingly, the true polarization potential v can be obtained by subtracting the electrode potential $V_2$ caused by a constant alternating current i from the electrode potential $V_1$ caused by a constant direct current $\underline{i}$.

Figure 1:
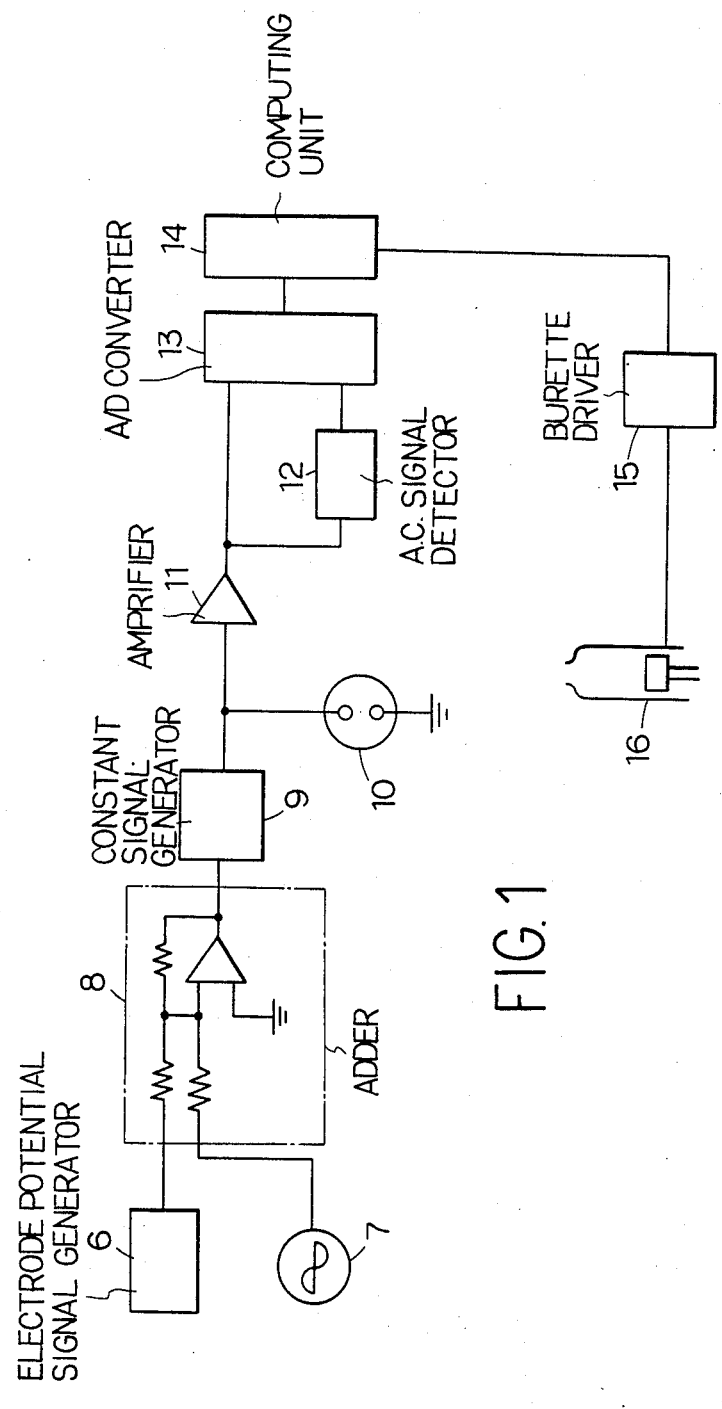
FIG. 1 is a block diagram showing one embodiment of a method of detecting an electrode potential according to the present invention.
Figure 2:
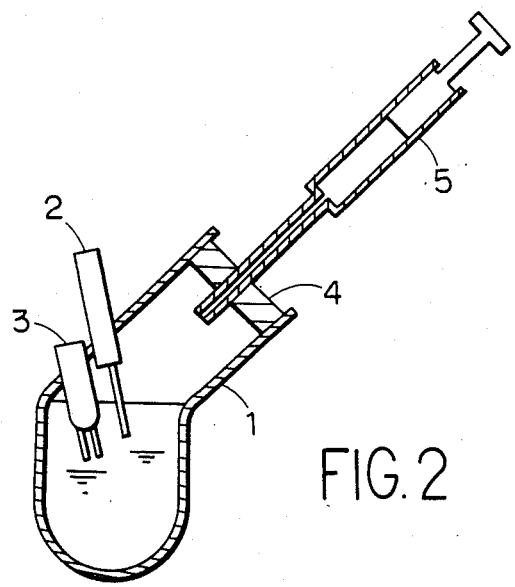
FIG. 2 is a schematic sectional view of the conventional vessel for use in a Karl Fischer moisture meter.
Figure 3:
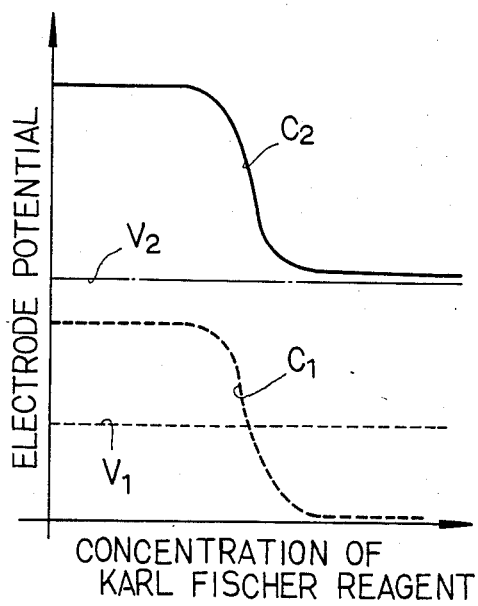
FIGS. 3 and 4 are graphs showing titration curve.
Figure 4:
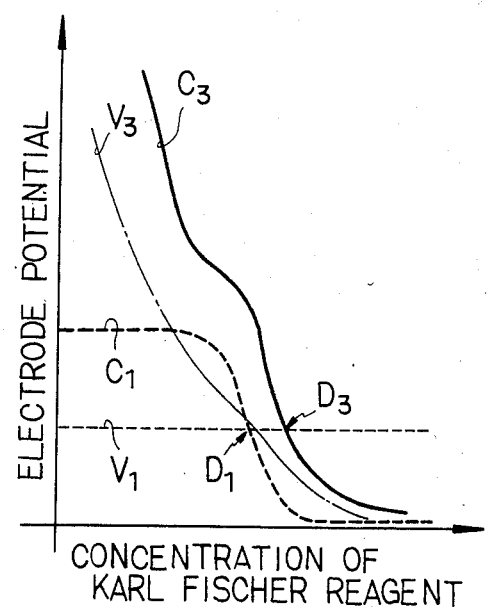

The embodiment of the present invention based on the above described measurement principle will now be described with reference to FIG. 1, wherein numeral 6 designates an electrode potential signal generator as a signal source for generating an electrode potential, numeral 7 designates an alternating current signal generator for generating an alternating current signal used for measuring a liquid resistance, numeral 8 designates an adder, numeral 9 designates a constant current circuit for giving a signal current to an electrode, numeral 10 designates a detecting electrode, numeral 11 designates an electrode potential detecting amplifier, numeral 12 designates an alternating current signal detector for detecting an alternating current signal used for measuring a liquid resistance, numeral 13 designates an A/D converter, numeral 14 designates a computing unit for calculating the true polarization potential and carrying out a titration control operation by subtracting a voltage drop due to a liquid resistance from an electrode potential, numeral 15 designates a burette-driver, and numeral 16 designates a burette of Karl Fischer reagent.

In operation, at first a signal for generating a potential in the detecting electrode 10 and an alternating current signal used for measuring a liquid resistance mix in the adder 8 are applied as a constant current source to the detecting electrode 10 through the constant current circuit 9. At this time, a potential generated in the detecting electrode 10 is detected by the electrode potential detecting amplifier 11, and of it an alternating current signal for measuring a liquid resistance is detected by the alternating current signal detector 12. The detected electrode potential and a potential resulting from the alternating current signal are converted into digital signals by means of the A/D converter 13 and transmitted to the computing unit 14 where the voltage drop due to a liquid resistance is subtracted from the electrode potential to calcuate the true polarization potential. In addition a signal is transmitted from the computing unit to the burette-driver 15 to control the run of Karl Fischer reagent into the burette 16 so that as the true polarization approaches the end point of titration, the titration slows down. The titration is thus controlled, ensuring exact detection of the end point potential of titration.

As described so far, according to the present invention, a constant current is passed through an end point detecting electrode in a Karl Fischer moisture determination apparatus and the true polarization potential is obtained by subtracting an electrode potential resulting from a liquid resistance of a liquid sample from the resulting electrode potential. As a consequence, the original titration curve showing the transformation of the liquid sample from a polarization state into a depolarization state can be obtained by titrating with Karl Fischer reagent, whereby the end point potential of titration can be detected exactly.

What is claimed is:

1. A method for determining the dead-stop end-point in a potentiometric Karl Fischer titration comprising:
    simultaneously imposing, upon a pair of electrodes immersed in a solution being determined, a direct current and an alternating current of constant amperages,
    determining by analysis of the voltage change in the alternating current the voltage change caused by the change in the resistance of the solution as Karl Fischer reagent is added,
    and subtracting said voltage change from the measured change in the direct current voltage to calculate the change in voltage which corresponds to the equivalence point in the titration.

2. The method according to claim 1, wherein the alternating current voltage is subtracted from the measured direct current voltage by a computing unit to provide an instantaneous readout of the corrected voltage.

3. The method according to claim 1, wherein the rate of addition of Karl Fischer reagent is controlled by an output signal from the computing unit to slow the rate of addition as the equivalence point is approached.

* * * * *